United States Patent [19]

Pluim et al.

[11] Patent Number: 5,326,405
[45] Date of Patent: Jul. 5, 1994

[54] SOLID LACTULOSE

[75] Inventors: Henk Pluim; Jan G. Kraaijenbrink, both of Weesp, Netherlands

[73] Assignee: Duphar International Research B.V., Weesp, Netherlands

[21] Appl. No.: 773,506

[22] Filed: Oct. 9, 1991

[30] Foreign Application Priority Data

Oct. 12, 1990 [EP] European Pat. Off. ........ 90202712.7

[51] Int. Cl.$^5$ ............................ C13F 1/00; C07H 3/00; C08B 37/00
[52] U.S. Cl. ........................................ 127/42; 127/58; 127/61; 536/124; 536/125
[58] Field of Search ............................. 127/61, 42, 58; 536/124, 125; 366/139

[56] References Cited

U.S. PATENT DOCUMENTS 5,003,061  3/1991  Carobbi et al. ..................... 127/58
5,004,057  4/1991  Binder et al. ......................... 127/61

FOREIGN PATENT DOCUMENTS 0318630  6/1989  European Pat. Off. ...... C13K 13/00
0333295  9/1989  European Pat. Off. ...... C07H 31/04

OTHER PUBLICATIONS

Chemical Abstracts, vol. 105, No. 16, Oct. 20, 1986, p. 107 Abstract No. 135841g, (& JP-A-61 104 800–Nikken Chem. Co.).
Patent Abstracts of Japan, vol. 14, No. 485, Oct. 23, 1990 (& JP-A-2 200 693–Morinaga Milk Ind. Co., Ltd.).

Primary Examiner—Theodore Morris
Assistant Examiner—P. L. Hailey
Attorney, Agent, or Firm—Stevens, Davis, Miller & Mosher

[57] ABSTRACT

The present invention is concerned with a method for the preparation of crystal-water-free crystalline lactulose by subjecting an aqeous solution or suspension of lactulose to simultaneous reduction of the water content by evaporation and continuous stirring, optionally in the presence of seed crystals, until a free-flowing solid powder is obtained.

4 Claims, No Drawings

SOLID LACTULOSE

The present invention is concerned with a method for the preparation of crystal-water-free crystalline lactulose.

Lactulose is a carbohydrate which can be obtained by isomerisation of lactose, which is usually carried out under alkaline conditions in aqueous solutions.

The compound has been proven to be pharmaceutically applicable due to its regulatory effect on the intestinal bacterial flora, particularly in portal systemic encephalopathy and dietary treatment of newborns.

Lactulose is prepared as a syrup which after purification can be administered. It would be more convenient, however, to provide a suitable dry form of lactulose, which e.g. can be packed in unit doses. The requirements for such a dry lactulose preparation are stability, high purity, absence of hygroscopicity.

Several dry forms of lactulose have been prepared. These can be classified according to the following main types:

- lactulose on solid carriers; suitable solid carriers for this purpose are vegetable fibers on which a lactulose syrup is applied (e.g. by spray-drying) or an adsorbent such as diatomaceous earth, adsorptive kaolin, activated lignin, adsorbent synthetic resin or active charcoal;
- amorphous lactulose which maybe obtained by accelerated or slow cooling of a concentrated syrup of lactulose, by spray-drying of the syrup, by caramelising of the syrup, or by drying lactulose foam;
- crystalline lactulose, which is generally obtained by crystallizing the sugar from an alcoholic solution. A serious draw-back of this type of solid lactulose is its content of organic solvent (generally methanol) in the crystals.

Lactulose may also be crystallized from an aqueous solution.

According to the Japanese Patent publication No. 61-104800 solid lactulose is prepared by concentration of a lactulose solution of more than 60% solid matter at a temperature between 60° and 110° C., subsequent addition of and thorough mixing with lactulose crystals to make up a final concentration of 94-98% and aging of the mixture at 35°-70° C. as long as required for complete solidification of the lactulose, typically for some 12-18 hours. In order to obtain a crystal-containing powder the solid lactulose should be broken up in an additional milling treatment.

In the European Patent publication No. 0 318 630 a very lengthy method is described wherein lactulose is crystallized at a temperature between 5° and 40° C. Apart from the lengthy procedure, up to 60 hours, another disadvantage is the low yield of the crystalline product (less than 70% of the lactulose present in solution actually crystallizes).

The present invention provides a fast method to completely convert the lactulose present in aqueous solution or suspension into a crystalline powder in a single preparation step.

According to the present invention the method is characterized by simultaneous continuous stirring and reduction of the water content by evaporation of an aqueous solution or suspension of lactulose, optionally in the presence of seed crystals, until a free-flowing solid powder is obtained.

The resulting powder completely consists of crystal-water-free lactulose and is non-hygroscopic.

The seed crystals which can be used according to the present invention preferably are composed of crystal-water-free lactulose.

The starting solution may have a low lactulose concentration which is increased during the process of reduction of the water content by evaporation and continued stirring. This reduction of the water content by evaporation preferably takes place under reduced pressure, in particular at a pressure of less than 200 mbar, more in particular at less than 100 mbar. The lactulose content based on total dry substance preferably can be at least 80% and more in particular can be at least 95%.

The optional addition of seed crystals should take place at a concentration and temperature where no substantial dissolution of the crystals takes place, preferably at a dry substance content in the solution of between 80% and 95%. If the starting solution already meets this latter requirement, the seed crystals may be present from the very outset.

The amount of seed crystals added depends on the product temperature and is also related to the content of dry substance in the lactulose solution.

Advantageously the content of seed crystals may amount to at least 1% of the total of dry constituents, preferably 1-5%. During the reduction of the water content by evaporation the product temperature should be maintained below the decomposition temperature of the lactulose, and preferably should not exceed 70°-80° C.

During the process the viscosity of the material increases dramatically, especially at the onset of the crystallization process. Therefore, a very powerful mixing equipment is required.

The reduction by evaporation and simultaneous mixing is continued until the total of the material is converted into a powder, and preferably until the water content is less than 1% by weight.

The crystalline lactulose powder prepared according to the present invention can be used for pharmaceutical purposes either in the form of a pharmaceutical composition or in the form of a food product, either for human or for veterinary applications.

EXAMPLE

Crystallization of lactulose 50 kg of lactulose syrup of an initial lactulose concentration of 65.3% by weight was concentrated in a drying equipment type MZA100 (Riniker) at reduced pressure lower than 0.2 bar (absolute) at a temperature less than 60° C. until a concentration of approximately 85% by weight, which took 100 minutes.

The solution so obtained was seeded with 2.4 kg of crystalline lactulose and the concentration by evaporation was continued for another 40 minutes at 65°-70° C. The end product was a white powder with a water content of 0.8%.

We claim:
1. A method for the preparation of water-free crystalline lactulose comprising simultaneously continuously stirring and reducing the water content by evaporation of an aqueous lactulose solution or lactulose suspension, optionally in the presence of seed crystals, until a free-flowing solid powder is obtained.
2. The method according to claim 1, wherein the content of seed crystals amounts to at least 1% of the total dry constituents.
3. The method according to claim 1, wherein the reduction by evaporation takes place under reduced pressure.
4. The method according to claim 1, wherein the reduction by evaporation is continued until the water content is less than 1% by weight.

* * * * *